United States Patent [19]

Amirdash

[11] Patent Number: 5,089,808
[45] Date of Patent: Feb. 18, 1992

[54] DEVICE GIVING WARNING WHEN UNDESIRED LIFTING POSITION IS ASSUMED

[75] Inventor: Omar S. Amirdash, Sunnyvale, Calif.

[73] Assignee: Amsau Company, Inc., Sunnyvale, Calif.

[21] Appl. No.: 603,511

[22] Filed: Oct. 26, 1990

[51] Int. Cl.$^5$ .............................. G08B 21/00
[52] U.S. Cl. .................... 340/573; 340/689; 340/693
[58] Field of Search .................. 340/573, 689, 693

[56] References Cited

U.S. PATENT DOCUMENTS

| | | | |
|---|---|---|---|
| 3,866,204 | 2/1975 | Barkley | 340/573 |
| 4,335,377 | 6/1982 | Bostic | 340/573 |
| 4,958,145 | 9/1990 | Morris | 340/573 |

Primary Examiner—Glen R. Swann, III
Attorney, Agent, or Firm—Flehr, Hohbach, Test, Albritton & Herbert

[57] ABSTRACT

A device giving warning when an undesired lifting position is assumed by a worker preparing to lift an object has a case having a longitudinal axis. A switch is mounted in the case and has operative and inoperative positions and assumes an operative position when the switch is tilted from the vertical beyond a predetermined angle. An alarm is carried by the case and electronic circuitry is connected to the tilt switch and to the alarm for actuating the alarm when the tilt switch is moved from the vertical beyond the predetermined position.

7 Claims, 2 Drawing Sheets

DEVICE GIVING WARNING WHEN UNDESIRED LIFTING POSITION IS ASSUMED

This invention relates to a device and method giving warning when an undesired lifting position is assumed by a human body and more particularly alerts a person to use his or her legs rather than his or her back in lifting or picking up an object.

Throughout the years, numerous back injuries have been sustained by individuals lifting objects improperly, that is, by utilizing the back rather than using the legs to do the lifting. Even though educational programs have been utilized to attempt to educate workers and others in the ways in which the lifting should be accomplished, this has not been completely satisfactory. Workers and others still continue to move objects improperly, often causing back injuries. When a worker does move something improperly, he often assumes an undesired lifting position which causes a back injury. Therefore, there is a need for a device that will alert workers when they are assuming an improper lifting position.

In general, it is an object of the present invention to provide a device and method which will give a warning to an individual when an undesired lifting position is assumed as represented by a back being bent beyond a predetermined angle from the vertical.

Another object of the invention is to provide a device of the above character which is very small so that is able to fit on the upper portion of a wearer, as for example, in the shirt pocket of the wearer.

Another object of the invention is to provide a device and a method in which an elapse of time occurs after the back is bent beyond the predetermined angle prior to a warning being given.

Another object of the invention is to provide a device of the above character which can be manufactured economically.

Another object of the invention is to provide a device of the above character which has a relatively long life.

Another object of the invention is to provide a device of the above character which is compact and lightweight.

Additional objects and features of the invention will appear from the following descriptions in which the preferred embodiment is set forth in conjunction with the accompanying drawings.

SUMMARY OF THE INVENTION

In general, the device giving a warning when an undesirable position is assumed consists of a case having a substantially vertical axis. A tilt switch is mounted in the casing and has operative and inoperative positions. The switch assumes an operative position when the switch is tilted from the vertical by more than a predetermined angle. An alarm is provided within the case. Circuitry is mounted in the housing and is connected to the tilt switch and activates the alarm after a predetermined time has elapsed after the tilt switch has assumed an operative position.

DESCRIPTION OF THE PREFERRED EMBODIMENT

Figure 5:
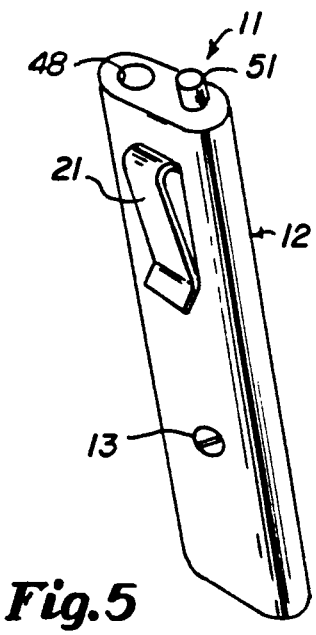
FIG. 5 is an isometric view of the device incorporating the present invention.

In particular, the device 11 of the present invention consists of a housing or case 12 formed of a suitable material such as plastic which is provided in two mating parts 12a and 12b. The case 12 can have suitable dimensions as for example a thickness of ⅜", a width of approximately 1⅛" and a height of approximately 4½". As shown in FIG. 5, the case 12 has a generally elongated configuration which in horizontal cross section has a rectangular configuration with rounded sides.

Part 12a is provided with upstanding bosses 13 and 14 and similarly, the part 12b is provided with upstanding bosses 16 and 17. The bosses 13 and 14 and 16 and 17 are spaced apart and are adapted to register with each other When the two parts 12a and 12b are mated. The two parts 12a and 12b are held together in a unitary assembly by screws 18 and 19 which extend from the part 12b through the bosses 16 and 17 in part 12a. The screw 18 is also utilized for securing a U-shaped spring metal clip 21 to the exterior of the case to facilitate clipping the device to the shirt pocket of a wearer as hereinafter described. The head of the screw 18 is disposed behind one leaf of the spring clip 21. The head of the other screw 19 is seated in a recess 22 provided in the exterior side of the part 12b.

A printed circuit board 26 is mounted within the case 12 and extends between the upper bosses 13 and 18 and the lower bosses 14 and 17. The printed circuit board 26 is provided with a hole 27 which fits the boss 16 and a slot 28 at the end thereof through which the boss 17 extends. The parts 12a and 12b of the case 12 are provided with small upstanding bosses 29 which fit into slots 30 provided in the printed circuit board 26 to support it in a stationary position within the case 12. The printed circuit board 26 carries its electrical components which are shown in the circuit diagram in FIG. 6.

A battery compartment 31 is provided within the case 12 below the lower extremity of the printed circuit board 26 and is adapted to receive a pair of conventional serially connected batteries B1 and B2 of a suitable type such as conventional A-type batteries. The batteries B1 and B2 engage interconnected coil springs 36 and 37 disposed against the bottom wall 38 of the case 12. L-shaped terminals 39 and 41 are adapted to engage the batteries B1 and B2 and are secured to the lower extremity of the printed circuit board 26 by rivets 42.

Figure 3:
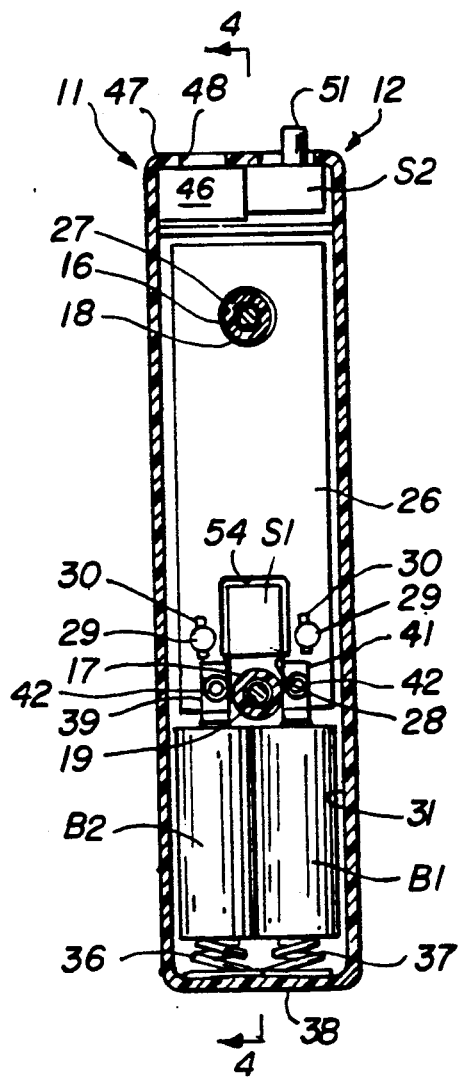
FIG. 3 is a cross-sectional view taken along the line 3—3 of FIG. 4 of a device incorporating the present invention.
Figure 4:
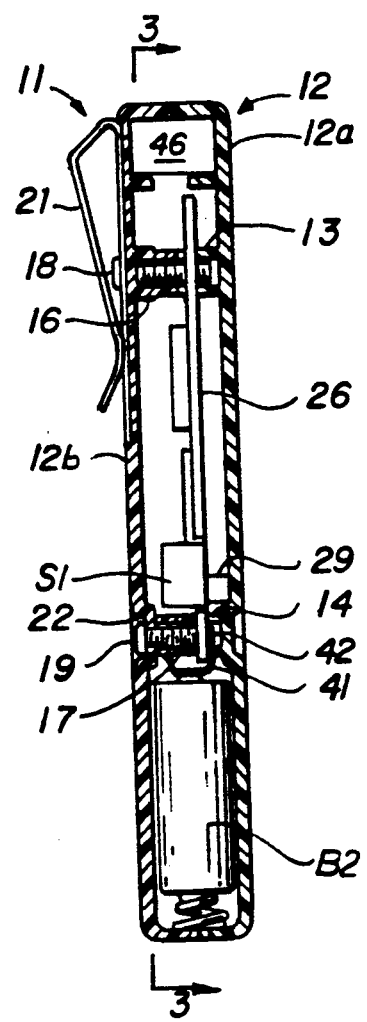
FIG. 4 is a cross sectional view taken along the lines 4—4 of FIG. 3.

A speaker 46 of conventional construction is mounted in case 12 adjacent the top wall 47 of the case 12 and above the printed circuit board 26 as shown particularly in FIG. 3. An opening 48 is provided in the top wall 47 through which sound emitted by speaker 46 can travel. An on/off switch S2 is also mounted in the case 12 in the upper extremity thereof and has a push button 51 which extends through the top wall 47 and is adapted to be engaged by the finger of the hand to turn the device on and off as hereinafter described.

A tilt switch S1 is mounted on the printed circuit board 26 and is seated within a U-shaped notch 54 provided in the printed circuit board so that the tilt switch is oriented and lies in a plane which is parallel to the plane of the printed circuit board 26 and which is centrally disposed to the longitudinal axis of the case 12.

Figure 6:
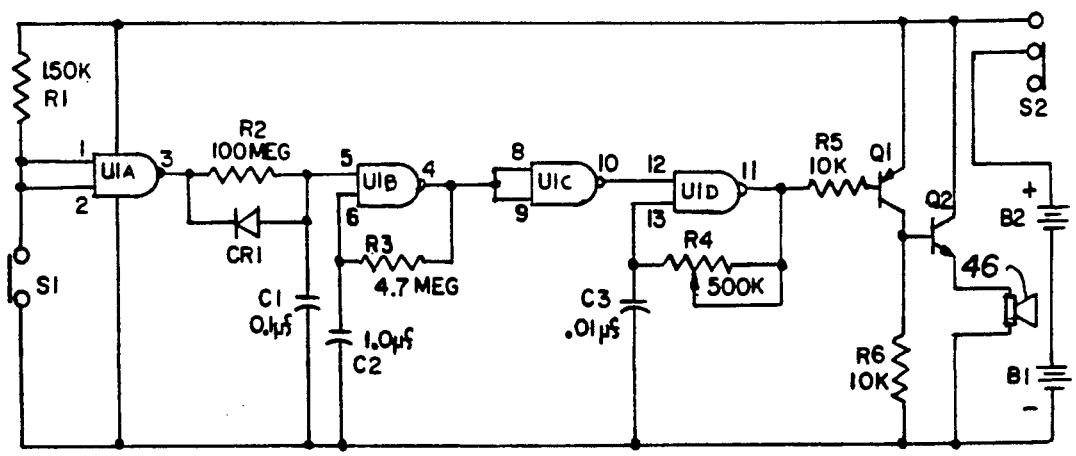
FIG. 6 is a circuit diagram of the circuitry utilized in the device of FIGS. 3, 4, and 5.

The electronic components which are utilized in the device are shown in FIG. 6. The tilt switch S1 is of a suitable type such as one manufactured by Pomus International of New Jersey and is identified as a Model CM1-0. It is a mercury type switch which is normally open when disposed in a vertical position and which will move to a closed position upon shifting at a certain angle from the vertical selected during manufacture. In the present invention, angle shifts have been set for 20° (highly sensitive), 55° (sensitive) and 75° (standard). However it should be appreciated that different predetermined angles can be utilized as for example angles ranging from 15° to 90°.

Let it be assumed that the batteries of B1 and B2 have a voltage of 1.5 volts each and thus when the switch S2 moved to the closed position, 3 volts are supplied to the circuitry shown in FIG. 6. These three volts are supplied through a 150K resistor R1 to the pins 1 and 2 of U1A to make those pins high with respect to pin 3. Let it be assumed that the switch S1 has been tilted beyond a predetermined angle so that it closes in a manner hereinafter described. Pins 1 and 2 of U1A then go low and pin 3 goes high to charge the 0.1 $\mu$f capacitor C1 through the 100 megohm resistor R2. The resistor R2 and the capacitor C1 form a time delay circuit which is set for a predetermined time, as for example, one second. If the switch S1 opens before this predetermined time, the capacitor C1 discharges through the diode CR1 to immediately discharge the capacitor C1.

Let it be assumed that the switch S1 is closed for a period of time greater than one second. When this occurs pin 6 on device U1B goes high which permits a positive feedback to be supplied from pin 4 through resistor R3 to the pin 5 of U1B to charge the 1.0 $\mu$f capacitor C2 to change the state of U1B. U1B is turned on and off to oscillate at a predetermined frequency as for example 1 hertz. The determining factors for the oscillator frequency is the size of the resistor R3 and the size of the capacitor C2. Thus, when the switch S1 is closed for a period of time greater than one second, the circuitry comprised of U1B, resistor R3 and the capacitor C2 can oscillate at the predetermined frequency of 1 hertz. This one hertz signal is inverted by U1C. The inverter U1C keeps U1B off when the switch S1 is opened. This is accomplished by sensing output 4 of U1B which is normally high when the switch S1 is on and it is desired to keep the input on 12 of U1D low to keep U1D off.

U1D serves as a high frequency oscillator and operates at a predetermined frequency as for example, two kilohertz. Its output pin 11 is connected through a variable 500K resistor R4 which is connected to the input pin 13 and is connected to one side of —0.01 $\mu$f capacitor C3. By the use of the variable resistor R4, the oscillator can be adjusted to be driven at an appropriate desired frequency, for example, two kilohertz. The output frequency is supplied from the pin 11 through the 10K resistor R5 to the base of a drive transistor Q1 which has its collector connected to the base of the transistor Q2 and to a 10K resistor R6. The resistor R6 serves as a base biasing resistor and serves to prevent leakage currents from turning on transistor Q2. The transistors Q1 and Q2 form a driver pair in which Q1 is a PNP transistor serving as an inverting driver and Q2 is NPN transistor serving as an emitter follower. The transistor Q2 drives the speaker 46 to supply a modulated two kilohertz tone modulated by the 1 hertz frequency provided by U1B to the speaker 46.

The circuitry used in FIG. 6 is CMOS circuitry which requires very little power to operate the same when the tilt switch S1 is not operated. The device with batteries has a weight of less than two ounces. U1A, U1B, U1C and U1D are devices in the form of a NAND Schmidt trigger circuit manufactured by RCA Model No. CD40903B.

Figure 1:
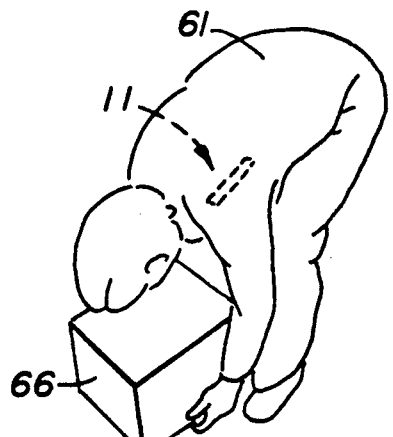
FIG. 1 is a perspective view of a worker wearing the device incorporating the present invention and assuming an improper lifting position for lifting an object.
Figure 2:
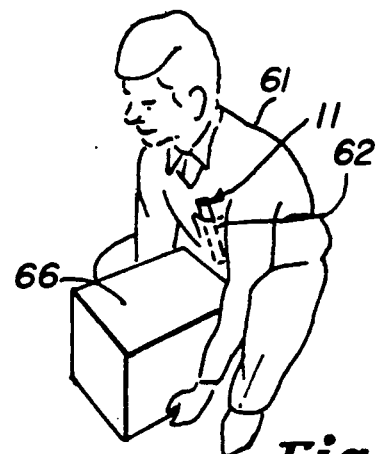
FIG. 2 is another perspective view of a worker wearing the device of the present invention and assuming a proper lifting position for lifting an object.

Operation and use of the device can now briefly be described as follows. Let it be assumed that a worker wishes to utilize the device. The worker 61 can take the device 11, turn it on by operating switch S2 and clipping the same into his shirt pocket 62 as shown in FIG. 2 using the spring clip 21. Let it be assumed that it is desired to pick up an object 66. The illustration in FIG. 1 shows a worker 61 improperly bending his back to pick up the package 61. As soon as the worker has bent his back from a normal vertical position through a suitable predetermined angle, as for example, 70°, the tilt switch S1 assumes a closed position. Assuming that this condition prevails for more than a predetermined time as for example one-half second provided by the timing circuit herein before described, the device will emit an audible beep in the form of a two kilohertz tone modulated at 1 hertz. This beeping sound will immediately notify the the wearer or the worker 61 that the worker has bent his back beyond the critical predetermined angle and that lifting should not be done from this position. This notifies the worker that he or she must assume the proper position for lifting the package 66 and keep his or her back in a relatively straight position and to bend the knees to lift the package 66, as shown in FIG. 2. When the lifting is done properly as shown in FIG. 2, the back is not bent beyond 70° and therefore the device will not emit its audible beep.

Thus, it can be seen that the device in the present invention solves a costly problem plaguing workers and employees throughout the world. It is believed that the present invention will greatly reduce the number of on the job back injuries which occur. The device will also help the workers to monitor their work habits to ensure that proper lifting positions are utilized for lifting articles.

Since the device is relatively small and lightweight, it can be worn by the worker without inconveniencing the worker. When it is not in use, the switch S2 can be turned off to conserve battery power. The device is constructed so that it is heavy duty and will function for long periods of time without the need for changing batteries. It is also constructed in such a manner that it can be manufactured at relatively low cost.

What is claimed is:

1. A device adapted to be inserted into the shirt pocket of a wearer giving warning when an undesired lifting position is assumed by a worker in the bending of the worker's back in preparing to lift an object, comprising an elongate case having a longitudinal axis and having a top wall, said case being of a size so that it can be placed in the shirt pocket of the wearer, a switch mounted in the case and having operative and inoperative positions and assuming an operative position when the switch is tilted from the vertical beyond a predetermined angle, an alarm carried by the case and electronic circuitry connected to the tilt switch and to the alarm for actuating the alarm when the tilt switch is moved from the vertical beyond said predetermined position, a clip secured to the outside of the case and extending below the top wall, and adapted to be secured to the shirt pocket of the wearer to prevent the device from falling out of the shirt pocket of the wearer while the worker is bending his back and an additional switch mounted in the case and extending through the top wall so that it is readily accessible to the wearer for operation of the same while the device is in the shirt pocket of the wearer, said additional switch being connected into said electronic circuitry for turning said electronic circuitry on and off.

2. A device as in claim 1 wherein said circuitry includes timing means for preventing a signal from being emitted by the alarm prior to the elapse of a predetermined time, during which time the tilt switch is in an operative position.

3. A device as in claim 2 wherein said circuitry includes an oscillator for generating an audible tone.

4. A device as in claim 3 wherein said circuitry includes an additional oscillator for modulating said audible tone.

5. A device as in claim 2 wherein said timing means of said timing circuitry includes a resistive/capacitive network and means for discharging said resistive/capacitive network.

6. A device as in claim 1 wherein said circuitry includes batteries and conductors connected to said batteries.

7. A device as in claim 1 wherein said alarm is in the form of an audible speaker.

* * * * *